(12) United States Patent
Budinger et al.

(10) Patent No.: US 11,915,570 B2
(45) Date of Patent: Feb. 27, 2024

(54) SYSTEM AND METHOD FOR CONCENTRATING GAS

(71) Applicant: Invacare Corporation, Elyria, OH (US)

(72) Inventors: Michael J. Budinger, Fairview Park, OH (US); Kevin R. Starkey, Centerville, OH (US)

(73) Assignee: Ventec Life Systems, Inc., Bothell, WA (US)

( * ) Notice: Subject to any disclaimer, the term of this patent is extended or adjusted under 35 U.S.C. 154(b) by 321 days.

(21) Appl. No.: 17/376,278

(22) Filed: Jul. 15, 2021

(65) Prior Publication Data

US 2022/0020258 A1   Jan. 20, 2022

Related U.S. Application Data

(60) Provisional application No. 63/052,533, filed on Jul. 16, 2020.

(51) Int. Cl.
*G08B 21/14* (2006.01)
*G01N 33/00* (2006.01)
(Continued)

(52) U.S. Cl.
CPC ........... *G08B 21/14* (2013.01); *B01D 53/047* (2013.01); *B01D 53/30* (2013.01);
(Continued)

(58) Field of Classification Search
CPC ........ G08B 21/14; G08B 5/36; B01D 53/047; B01D 53/30; B01D 2253/108;
(Continued)

(56) References Cited

U.S. PATENT DOCUMENTS

| 4,127,395 A | 11/1978 | McKey et al. |
| 4,144,037 A | 3/1979 | Armond et al. |

(Continued)

FOREIGN PATENT DOCUMENTS

| AU | 1999015998 A | 8/1999 |
| AU | 200072682 A1 | 5/2001 |

(Continued)

OTHER PUBLICATIONS

US 6,979,301 B2, 12/2005, Van Brunt et al. (withdrawn)

(Continued)

*Primary Examiner* — Ojiako K Nwugo
(74) *Attorney, Agent, or Firm* — Calfee, Halter & Griswold LLP

(57) ABSTRACT

Systems and methods are provided for displaying status of a gas concentrator. The systems and methods include, for example, a display having a plurality of illuminable segments. The illuminable segments can be illuminated to form one or more displays indicating system status. The system status includes, for example, warmup, normal operation, low priority alarm(s), high-priority alarms, etc. In one embodiment, the systems and methods also read oxygen values of the gas concentrating system as one basis for determining system status. Other bases are also disclosed.

20 Claims, 6 Drawing Sheets

(51) Int. Cl.
   *B01D 53/30* (2006.01)
   *B01D 53/047* (2006.01)
(52) U.S. Cl.
   CPC ... *G01N 33/0063* (2013.01); *B01D 2253/108* (2013.01); *B01D 2256/12* (2013.01); *B01D 2257/102* (2013.01); *B01D 2257/502* (2013.01); *B01D 2257/504* (2013.01); *B01D 2257/80* (2013.01); *B01D 2259/40009* (2013.01)
(58) Field of Classification Search
   CPC .......... B01D 2256/12; B01D 2257/102; B01D 2257/502; B01D 2257/504; B01D 2257/80; B01D 2259/40009; B01D 2258/06; B01D 2259/40007; B01D 2259/4533; G01N 33/0063; Y02C 20/40
   See application file for complete search history.

(56) References Cited

U.S. PATENT DOCUMENTS

| | | | |
|---|---|---|---|
| 4,247,311 A | 1/1981 | Seibert | |
| 4,378,982 A | 4/1983 | Mcombs | |
| 4,449,990 A | 5/1984 | Tedford | |
| 4,454,596 A | 6/1984 | Wunsch et al. | |
| 4,561,287 A | 12/1985 | Rowland | |
| 4,575,042 A | 3/1986 | Grimland | |
| 4,648,888 A | 3/1987 | Rowland | |
| 4,826,510 A | 5/1989 | McCombs | |
| 4,832,711 A | 5/1989 | Christel, Jr. et al. | |
| 4,932,402 A | 6/1990 | Snook et al. | |
| 4,971,609 A | 11/1990 | Pawlos | |
| 5,057,822 A | 10/1991 | Hoffman | |
| 5,099,837 A | 3/1992 | Russel et al. | |
| 5,101,656 A | 4/1992 | Miller | |
| 5,144,945 A | 8/1992 | Nishino et al. | |
| 5,258,056 A | 11/1993 | Shirley et al. | |
| 5,294,049 A | 3/1994 | Trunkle et al. | |
| 5,298,226 A | 3/1994 | Nowobilski | |
| 5,469,372 A | 11/1995 | McBrearty et al. | |
| 5,474,595 A | 12/1995 | McCombs | |
| 5,593,478 A | 1/1997 | Hill et al. | |
| 5,626,131 A | 5/1997 | Chua et al. | |
| 5,680,409 A | 10/1997 | Qin et al. | |
| 5,720,276 A | 2/1998 | Kobatake et al. | |
| 5,779,773 A | 7/1998 | Cam et al. | |
| 5,785,681 A | 7/1998 | Indravudh | |
| 5,906,672 A | 5/1999 | Michaels et al. | |
| 5,917,135 A | 6/1999 | Michaels et al. | |
| 5,931,160 A | 8/1999 | Gilmore et al. | |
| 5,988,165 A | 11/1999 | Richey, II et al. | |
| 6,051,051 A | 4/2000 | Hees et al. | |
| 6,106,245 A | 8/2000 | Cabuz | |
| 6,151,586 A | 11/2000 | Brown | |
| 6,152,134 A | 11/2000 | Webber et al. | |
| 6,266,995 B1 | 7/2001 | Scott | |
| 6,279,377 B1 | 8/2001 | Cao | |
| 6,427,690 B1 | 8/2002 | McCombs et al. | |
| 6,442,433 B1 | 8/2002 | Linberg | |
| 6,472,988 B1 | 10/2002 | Feld et al. | |
| 6,517,610 B1 | 2/2003 | La Houssaye | |
| 6,520,176 B1 | 2/2003 | Dubois et al. | |
| 6,561,187 B2 | 5/2003 | Schmidt et al. | |
| 6,629,525 B2 | 10/2003 | Hill et al. | |
| 6,651,658 B1 | 11/2003 | Hill et al. | |
| 6,691,702 B2 | 2/2004 | Appel et al. | |
| 6,764,534 B2 | 7/2004 | McCombs et al. | |
| 6,837,244 B2 | 1/2005 | Yagi et al. | |
| 6,878,186 B2 | 4/2005 | Neary | |
| 6,949,133 B2 | 9/2005 | McCombs et al. | |
| 6,962,654 B2 | 11/2005 | Arnaud | |
| 7,036,729 B2 | 5/2006 | Chung | |
| 7,115,104 B2 | 10/2006 | Van Brunt et al. | |
| 7,278,983 B2 | 10/2007 | Ireland et al. | |
| 7,294,170 B2 | 11/2007 | Richey, II et al. | |
| 7,306,657 B2 | 12/2007 | Yagi et al. | |
| 7,329,304 B2 | 2/2008 | Bliss et al. | |
| 7,331,340 B2 | 2/2008 | Barney | |
| 7,393,382 B2 | 7/2008 | Givens | |
| 7,425,203 B2 | 9/2008 | Van Brunt et al. | |
| 7,431,032 B2 | 10/2008 | Jagger et al. | |
| 7,445,663 B1 | 11/2008 | Hunter et al. | |
| 7,455,717 B2 | 11/2008 | Sprinkle | |
| 7,491,182 B2 | 2/2009 | Van Brunt | |
| 7,505,374 B2 * | 3/2009 | Booty, Jr. | G04G 9/02 368/239 |
| 7,552,731 B2 | 6/2009 | Jorczak et al. | |
| 7,604,004 B2 | 10/2009 | Jagger et al. | |
| 7,604,005 B2 | 10/2009 | Jagger et al. | |
| 7,652,571 B2 | 1/2010 | Parkulo et al. | |
| 7,662,638 B2 | 2/2010 | Dadala et al. | |
| 7,686,870 B1 | 3/2010 | Deane et al. | |
| 7,722,698 B2 | 5/2010 | Thompson et al. | |
| 7,722,700 B2 | 5/2010 | Sprinkle | |
| 7,753,996 B1 | 7/2010 | Deane et al. | |
| 7,766,010 B2 | 8/2010 | Jagger et al. | |
| 7,794,522 B2 | 9/2010 | Bliss et al. | |
| 7,826,728 B2 | 11/2010 | Konno et al. | |
| 7,866,315 B2 | 1/2011 | Jagger et al. | |
| 7,875,105 B2 | 1/2011 | Chambers et al. | |
| 7,922,789 B1 | 4/2011 | Deane et al. | |
| 7,931,197 B2 | 4/2011 | Brandt et al. | |
| 8,013,739 B2 | 9/2011 | Parkulo et al. | |
| 8,062,003 B2 | 11/2011 | Goertzen et al. | |
| 8,070,853 B2 | 12/2011 | Sprinkle | |
| 8,092,396 B2 | 1/2012 | Bagha et al. | |
| 8,231,541 B2 | 7/2012 | Colquitt et al. | |
| 8,262,771 B2 | 9/2012 | Seki et al. | |
| 8,366,402 B2 | 2/2013 | St. Michel | |
| 8,366,815 B2 | 2/2013 | Taylor et al. | |
| 8,377,181 B2 | 2/2013 | Taylor et al. | |
| 8,421,465 B2 | 4/2013 | Carter | |
| 8,547,062 B2 | 10/2013 | Carter et al. | |
| 8,568,519 B2 | 10/2013 | Taylor et al. | |
| 8,599,016 B2 | 12/2013 | Parkulo et al. | |
| 8,668,767 B2 | 3/2014 | Sprinkle et al. | |
| 8,677,998 B2 | 3/2014 | Yamaura et al. | |
| 8,726,744 B2 | 5/2014 | Alburty et al. | |
| 8,818,824 B2 | 8/2014 | DeBusk et al. | |
| 8,956,289 B2 | 2/2015 | Kitajima et al. | |
| 9,058,741 B2 | 6/2015 | Steinhauer et al. | |
| 9,072,849 B2 | 7/2015 | Steinhauer et al. | |
| 9,132,377 B2 | 9/2015 | Richey, II et al. | |
| 9,266,053 B2 | 2/2016 | Shelnutt et al. | |
| 9,317,660 B2 | 4/2016 | Burich et al. | |
| 9,327,090 B2 | 5/2016 | Steinhauer et al. | |
| 9,352,110 B2 | 5/2016 | Steinhauer et al. | |
| 9,364,626 B2 | 6/2016 | Carter et al. | |
| 9,440,179 B2 | 9/2016 | Wilkinson et al. | |
| 9,460,262 B2 | 10/2016 | Kaufman et al. | |
| 9,462,977 B2 | 10/2016 | Horseman | |
| 9,693,734 B2 | 7/2017 | Horseman | |
| 9,714,860 B2 | 7/2017 | Obenchain | |
| 9,763,585 B2 | 9/2017 | Addison et al. | |
| 9,782,557 B2 | 10/2017 | Wilkinson et al. | |
| 9,788,735 B2 | 10/2017 | Al-Ali | |
| 9,808,156 B2 | 11/2017 | Horseman | |
| 9,833,142 B2 | 12/2017 | Horseman | |
| 9,838,508 B2 | 12/2017 | Salem | |
| 9,839,786 B2 | 12/2017 | Rondoni et al. | |
| 9,872,623 B2 | 1/2018 | Al-Ali | |
| 9,872,965 B2 | 1/2018 | Baloa Welzien et al. | |
| 9,956,370 B2 | 5/2018 | Wilkinson et al. | |
| 9,957,125 B2 | 5/2018 | Ray | |
| 9,990,466 B2 | 6/2018 | DeBusk et al. | |
| 10,004,435 B2 | 6/2018 | Larvenz et al. | |
| 10,010,969 B2 | 7/2018 | Reed et al. | |
| 10,037,044 B2 | 7/2018 | Laberge et al. | |
| 10,058,269 B2 | 8/2018 | Lynn | |
| 10,108,785 B2 | 10/2018 | Kamen et al. | |
| 10,139,282 B2 | 11/2018 | Chrostowski | |
| 10,148,912 B1 * | 12/2018 | Oliver | H04M 3/563 |
| 10,179,217 B2 | 1/2019 | Steinhauer et al. | |

(56) References Cited

U.S. PATENT DOCUMENTS

| | | |
|---|---|---|
| 10,252,037 B2 | 4/2019 | Degen et al. |
| 10,271,779 B2 | 4/2019 | Addison et al. |
| 10,349,901 B2 | 7/2019 | Osypka et al. |
| 10,357,628 B2 | 7/2019 | Jagger et al. |
| 10,391,019 B2 | 8/2019 | Stryker et al. |
| 10,426,904 B2 | 10/2019 | Broborg et al. |
| 10,496,788 B2 | 12/2019 | Amarasingham et al. |
| 10,521,720 B2 | 12/2019 | Detzler et al. |
| 10,592,637 B2 | 3/2020 | Velamuri et al. |
| 10,630,814 B2 | 4/2020 | Barnes et al. |
| 10,753,598 B2 * | 8/2020 | Chien ................ F21V 33/0004 |
| 10,948,175 B2 * | 3/2021 | Chien ................ F21V 33/0004 |
| 2002/0053286 A1 | 5/2002 | Czabala |
| 2002/0096174 A1 | 7/2002 | Hill et al. |
| 2003/0068828 A1 | 4/2003 | Dadala et al. |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2004/0167464 A1 | 8/2004 | Ireland et al. |
| 2005/0259088 A1 * | 11/2005 | Ogasawara ............ B60K 37/06<br>345/184 |
| 2005/0263199 A1 | 12/2005 | Meheen |
| 2006/0005842 A1 | 1/2006 | Rashad |
| 2006/0025932 A1 | 2/2006 | Dadala et al. |
| 2006/0086251 A1 | 4/2006 | Sprinkle |
| 2006/0092768 A1 * | 5/2006 | Demas ..................... G04G 9/00<br>368/21 |
| 2006/0092769 A1 * | 5/2006 | Demas .................. G04B 19/22<br>368/82 |
| 2006/0174871 A1 | 8/2006 | Jagger et al. |
| 2006/0174872 A1 | 8/2006 | Jagger |
| 2006/0219245 A1 | 10/2006 | Holder |
| 2006/0220881 A1 | 10/2006 | Al et al. |
| 2006/0227123 A1 * | 10/2006 | Bychkov .............. H05K 5/0278<br>345/204 |
| 2006/0230768 A1 * | 10/2006 | Huber .................. F25D 21/008<br>62/157 |
| 2006/0230929 A1 | 10/2006 | Bliss et al. |
| 2006/0251408 A1 | 11/2006 | Konno et al. |
| 2007/0056584 A1 | 3/2007 | Jagger et al. |
| 2007/0140869 A1 | 6/2007 | St. Michel |
| 2007/0144519 A1 | 6/2007 | Henry et al. |
| 2007/0250017 A1 | 10/2007 | Carred et al. |
| 2008/0007396 A1 | 1/2008 | Parkulo et al. |
| 2008/0066616 A1 | 3/2008 | Sprinkle |
| 2008/0136652 A1 | 6/2008 | Vaisnys et al. |
| 2008/0165629 A1 * | 7/2008 | Billeaudeaux ............ G04G 9/02<br>368/82 |
| 2008/0174871 A1 | 8/2008 | Jagger et al. |
| 2008/0238323 A1 | 10/2008 | Chan et al. |
| 2008/0246277 A1 | 10/2008 | Gallagher et al. |
| 2008/0257145 A1 | 10/2008 | Sprinkle |
| 2008/0262657 A1 | 10/2008 | Howell et al. |
| 2008/0294348 A1 * | 11/2008 | Tanaka ................. A61B 5/7445<br>702/19 |
| 2009/0065526 A1 | 3/2009 | Sprinkle |
| 2009/0118632 A1 | 5/2009 | Goepp |
| 2009/0126736 A1 | 5/2009 | Taylor et al. |
| 2009/0209839 A1 | 8/2009 | Ochs et al. |
| 2009/0211438 A1 | 8/2009 | Thompson et al. |
| 2009/0211448 A1 | 8/2009 | McClain |
| 2009/0216747 A1 | 8/2009 | Li et al. |
| 2009/0232706 A1 | 9/2009 | Dadala et al. |
| 2009/0316533 A1 * | 12/2009 | Liu ..................... G04G 15/006<br>368/10 |
| 2010/0071698 A1 | 3/2010 | Kiritake |
| 2010/0095841 A1 | 4/2010 | Naheiri |
| 2010/0106458 A1 | 4/2010 | Leu |
| 2010/0114218 A1 | 5/2010 | Heath |
| 2010/0146426 A1 | 6/2010 | Parkulo et al. |
| 2010/0214877 A1 * | 8/2010 | Turk ..................... A61J 7/0481<br>368/10 |
| 2010/0242734 A1 | 9/2010 | Maeda et al. |
| 2010/0253505 A1 | 10/2010 | Chou |
| 2010/0294127 A1 | 11/2010 | Dolensky |
| 2011/0017216 A1 | 1/2011 | Van Brunt et al. |
| 2011/0056904 A1 | 3/2011 | Rozenberg |
| 2011/0073107 A1 | 3/2011 | Rodman et al. |
| 2011/0080348 A1 * | 4/2011 | Lin ....................... G06F 1/1626<br>345/1.3 |
| 2011/0126829 A1 | 6/2011 | Carter |
| 2011/0128008 A1 | 6/2011 | Carter |
| 2011/0148773 A1 * | 6/2011 | Rudolph ................ H03K 17/96<br>345/173 |
| 2011/0148775 A1 * | 6/2011 | Rudolph .................. F24C 7/086<br>345/35 |
| 2011/0211425 A1 * | 9/2011 | Liu ....................... G04G 15/006<br>368/10 |
| 2011/0260850 A1 * | 10/2011 | Ringenwald ........... B60K 35/00<br>340/461 |
| 2011/0315140 A1 | 12/2011 | Shuman |
| 2012/0036461 A1 | 2/2012 | Parkulo et al. |
| 2012/0122545 A1 * | 5/2012 | Watkins .............. G07F 17/3211<br>463/20 |
| 2013/0012788 A1 | 1/2013 | Horseman |
| 2013/0012789 A1 | 1/2013 | Horseman |
| 2013/0012790 A1 | 1/2013 | Horseman |
| 2013/0233168 A1 | 9/2013 | Richey, II |
| 2013/0264218 A1 | 10/2013 | Vinton et al. |
| 2013/0297330 A1 | 11/2013 | Kamen et al. |
| 2013/0333702 A1 | 12/2013 | Baloa et al. |
| 2014/0000604 A1 | 1/2014 | Steinhauer et al. |
| 2014/0000605 A1 | 1/2014 | Steinhauer et al. |
| 2014/0000607 A1 | 1/2014 | Steinhauer et al. |
| 2014/0000608 A1 | 1/2014 | Steinhauer et al. |
| 2014/0000609 A1 | 1/2014 | Steinhauer et al. |
| 2014/0002246 A1 | 1/2014 | Steinhauer et al. |
| 2014/0006041 A1 | 1/2014 | Steinhauer et al. |
| 2014/0006052 A1 | 1/2014 | Steinhauer et al. |
| 2014/0007405 A1 | 1/2014 | Chambers et al. |
| 2014/0049792 A1 | 2/2014 | Ha |
| 2014/0163335 A1 | 6/2014 | Horseman |
| 2014/0163336 A1 | 6/2014 | Horseman |
| 2014/0163337 A1 | 6/2014 | Horseman |
| 2014/0166003 A1 | 6/2014 | Van Brunt et al. |
| 2014/0188516 A1 | 7/2014 | Kamen et al. |
| 2014/0190348 A1 | 7/2014 | Richey, II et al. |
| 2014/0343854 A1 * | 11/2014 | Wollard ................. G09F 13/04<br>702/3 |
| 2015/0077245 A1 | 3/2015 | Kaufman et al. |
| 2015/0164390 A1 | 6/2015 | Larvenz et al. |
| 2015/0174359 A1 | 6/2015 | Elliott et al. |
| 2015/0213224 A1 | 7/2015 | Amarasingham et al. |
| 2015/0234993 A1 | 8/2015 | Detzler et al. |
| 2015/0250960 A1 | 9/2015 | Broberg et al. |
| 2015/0362929 A1 | 12/2015 | Laberge et al. |
| 2016/0022971 A1 | 1/2016 | Degen et al. |
| 2016/0152430 A1 | 6/2016 | Ray |
| 2016/0189345 A1 * | 6/2016 | Fujita ..................... B60K 35/00<br>345/660 |
| 2016/0206838 A1 | 7/2016 | Steinhauer et al. |
| 2016/0275261 A1 | 9/2016 | Velamuri et al. |
| 2016/0303388 A1 | 10/2016 | Rondoni |
| 2016/0324425 A1 | 11/2016 | Addison et al. |
| 2016/0367197 A1 | 12/2016 | Addison et al. |
| 2016/0371479 A1 * | 12/2016 | Wynen ................. H04L 63/083 |
| 2016/0375218 A1 | 12/2016 | Sprinkle et al. |
| 2016/0378067 A1 * | 12/2016 | Bishop ..................... G04G 9/06<br>368/241 |
| 2017/0000395 A1 | 1/2017 | Addison et al. |
| 2017/0000423 A1 | 1/2017 | Addison et al. |
| 2017/0011131 A1 | 1/2017 | Li et al. |
| 2017/0017767 A1 | 1/2017 | Flower et al. |
| 2017/0053077 A1 | 2/2017 | Osypka et al. |
| 2017/0063456 A1 * | 3/2017 | Yamasaki ............... G06V 20/20 |
| 2017/0080262 A1 | 3/2017 | Freres et al. |
| 2017/0117444 A1 * | 4/2017 | Stoll ..................... H01L 33/504 |
| 2017/0119235 A1 | 5/2017 | Hyde et al. |
| 2017/0202728 A1 | 7/2017 | Stryker |
| 2017/0221414 A1 | 8/2017 | Endo |
| 2017/0224231 A1 | 8/2017 | Al-Ali |

(56) References Cited

U.S. PATENT DOCUMENTS

| | | | |
|---|---|---|---|
| 2017/0224233 | A1 | 8/2017 | Al-Ali |
| 2017/0291708 | A1 | 10/2017 | Buenting et al. |
| 2018/0014791 | A1 | 1/2018 | Montgomery et al. |
| 2018/0156667 | A1 | 6/2018 | Chrostowski |
| 2018/0192965 | A1 | 7/2018 | Rose et al. |
| 2018/0271421 | A1 | 9/2018 | Larvenz et al. |
| 2018/0279475 | A1* | 9/2018 | Kloth .................... H01L 33/62 |
| 2018/0314416 | A1 | 11/2018 | Powderly et al. |
| 2018/0369532 | A1 | 12/2018 | Nebrigic |
| 2019/0068760 | A1 | 2/2019 | Barnes et al. |
| 2019/0134340 | A1 | 5/2019 | Nebrigac |
| 2019/0143056 | A1 | 5/2019 | Steinhauer et al. |
| 2019/0200577 | A1 | 7/2019 | Kath |
| 2019/0295718 | A1* | 9/2019 | Lawhorn ................ A61M 1/96 |
| 2019/0341793 | A1* | 11/2019 | Chien .................... F21V 33/00 |
| 2019/0374139 | A1 | 12/2019 | Kiani et al. |
| 2020/0016605 | A1 | 1/2020 | Nebrigac |
| 2020/0035348 | A1 | 1/2020 | Sartor et al. |
| 2020/0060545 | A1 | 2/2020 | Maher et al. |
| 2020/0064011 | A1 | 2/2020 | Nakano |
| 2020/0081856 | A1 | 3/2020 | Kojima |
| 2020/0146442 | A1* | 5/2020 | Rutzke .................... A47B 21/04 |
| 2020/0264031 | A1* | 8/2020 | Lease .................... G01F 23/38 |
| 2021/0366320 | A1* | 11/2021 | Wang .................... H10K 77/111 |

FOREIGN PATENT DOCUMENTS

| | | |
|---|---|---|
| AU | 748829 B2 | 6/2002 |
| AU | 200072387 A | 6/2002 |
| AU | 2008240038 A1 | 10/2009 |
| AU | 2010282150 A1 | 7/2012 |
| AU | 2012279039 A1 | 1/2014 |
| AU | 2012279044 A1 | 1/2014 |
| AU | 2012279110 A1 | 1/2014 |
| AU | 2013364131 | 6/2014 |
| AU | 2013364131 A1 | 7/2015 |
| AU | 2013364131 A8 | 9/2015 |
| AU | 2013364131 A2 | 10/2015 |
| AU | 2014357428 B2 | 5/2019 |
| AU | 2013364131 B2 | 7/2019 |
| AU | 2018258679 A1 | 11/2019 |
| AU | 2018295533 A1 | 1/2020 |
| BR | 112015015024 A2 | 7/2017 |
| CA | 2310667 A1 | 6/1999 |
| CA | 2379697 A1 | 2/2001 |
| CA | 2438457 | 2/2004 |
| CA | 2772539 A1 | 6/2004 |
| CA | 2683367 A1 | 10/2008 |
| CA | 2506292 C | 5/2012 |
| CA | 2839287 A1 | 1/2013 |
| CA | 2840969 A1 | 1/2013 |
| CA | 2840975 A1 | 1/2013 |
| CA | 2840984 A1 | 1/2013 |
| CA | 3016496 A1 | 1/2013 |
| CA | 2310667 C | 7/2013 |
| CA | 2772539 C | 4/2014 |
| CA | 2896086 A1 | 6/2014 |
| CA | 2933599 A1 | 6/2015 |
| CA | 2945137 A1 | 10/2015 |
| CA | 2982855 A1 | 11/2016 |
| CA | 2840979 C | 7/2018 |
| CA | 3050643 A1 | 7/2018 |
| CA | 3059209 A1 | 11/2018 |
| CA | 3069278 A1 | 1/2019 |
| CA | 2933599 C | 12/2019 |
| CA | 3016496 C | 1/2020 |
| CN | 87102164 | 11/1987 |
| CN | 2585215 Y | 11/2003 |
| CN | 1610516 A | 4/2005 |
| CN | 1697681 A | 11/2005 |
| CN | 1697682 A | 11/2005 |
| CN | 1780655 A | 5/2006 |
| CN | 2839861 | 11/2006 |
| CN | 101506868 A | 8/2009 |
| CN | 101520690 A | 9/2009 |
| CN | 101681455 A | 3/2010 |
| CN | 101687134 A | 3/2010 |
| CN | 101873824 A | 10/2010 |
| CN | 1780655 B | 12/2010 |
| CN | 101520690 B | 7/2011 |
| CN | 101141567 B | 12/2012 |
| CN | 103448727 A | 12/2013 |
| CN | 103534664 A | 1/2014 |
| CN | 101543047 B | 2/2014 |
| CN | 103764021 A | 4/2014 |
| CN | 103781405 A | 5/2014 |
| CN | 103781409 A | 5/2014 |
| CN | 104235038 A | 12/2014 |
| CN | 204226229 U | 3/2015 |
| CN | 104951225 | 9/2015 |
| CN | 104951225 A | 9/2015 |
| CN | 104969227 A | 10/2015 |
| CN | 105269352 A | 1/2016 |
| CN | 205237581 U | 5/2016 |
| CN | 205302544 U | 6/2016 |
| CN | 205344448 U | 6/2016 |
| CN | 205578301 U | 9/2016 |
| CN | 106075696 A | 11/2016 |
| CN | 106102571 A | 11/2016 |
| CN | 106455927 A | 2/2017 |
| CN | 103477340 B | 3/2017 |
| CN | 106574784 A | 4/2017 |
| CN | 106793238 A | 5/2017 |
| CN | 106887110 A | 6/2017 |
| CN | 106913326 A | 7/2017 |
| CN | 106931478 A | 7/2017 |
| CN | 206459246 U | 9/2017 |
| CN | 206655848 U | 11/2017 |
| CN | 108348148 A | 7/2018 |
| CN | 105373219 B | 9/2018 |
| CN | 109171755 A | 1/2019 |
| CN | 110292696 A | 10/2019 |
| CN | 110431509 A | 11/2019 |
| CN | 110604580 A | 12/2019 |
| CN | 107430497 B | 3/2020 |
| CN | 111792030 A | 10/2020 |
| DE | 3723019 A1 | 1/1989 |
| DE | 29605889 U1 | 6/1996 |
| DE | 19936893 A1 | 2/2001 |
| DE | 10037227 A1 | 2/2002 |
| DE | 19936893 C2 | 8/2002 |
| DE | 102005042268 A1 | 5/2006 |
| DE | 102007021564 A1 | 11/2008 |
| DE | 202006020670 U1 | 7/2009 |
| DE | 102008016768 A1 | 10/2009 |
| DE | 102008030790 A1 | 12/2009 |
| DE | 102014103377 A1 | 9/2014 |
| DE | 102014103397 A1 | 9/2014 |
| DE | 102016116761 A1 | 3/2017 |
| DE | 102017204049 B3 | 5/2018 |
| DE | 102018115858 A1 | 1/2020 |
| EP | 0420620 A2 | 4/1991 |
| EP | 0885645 A2 | 12/1998 |
| EP | 1032906 A1 | 9/2000 |
| EP | 1157731 A1 | 11/2001 |
| EP | 0885645 B1 | 1/2005 |
| EP | 1661596 B1 | 5/2006 |
| EP | 1707928 A1 | 10/2006 |
| EP | 1895892 A1 | 3/2008 |
| EP | 1340071 B1 | 3/2009 |
| EP | 2136682 A1 | 12/2009 |
| EP | 2138060 A2 | 12/2009 |
| EP | 2197530 A2 | 6/2010 |
| EP | 2266093 A2 | 12/2010 |
| EP | 2729052 A1 | 5/2014 |
| EP | 2729054 A1 | 5/2014 |
| EP | 2729056 A1 | 5/2014 |
| EP | 2751751 A1 | 7/2014 |
| EP | 2773410 A1 | 9/2014 |
| EP | 2861139 A1 | 4/2015 |
| EP | 2895224 A1 | 7/2015 |
| EP | 0936362 A2 | 10/2015 |
| EP | 1636076 B1 | 12/2015 |
| EP | 2613838 B1 | 3/2016 |

(56) References Cited

FOREIGN PATENT DOCUMENTS

| | | |
|---|---|---|
| EP | 2138060 B1 | 6/2016 |
| EP | 3069279 A1 | 9/2016 |
| EP | 3082977 A2 | 10/2016 |
| EP | 3117355 A1 | 1/2017 |
| EP | 3129949 A2 | 2/2017 |
| EP | 1850917 B1 | 6/2017 |
| EP | 3282382 A1 | 2/2018 |
| EP | 3283165 A1 | 2/2018 |
| EP | 3286910 A1 | 2/2018 |
| EP | 3294120 A1 | 3/2018 |
| EP | 3316769 A1 | 5/2018 |
| EP | 3316770 A1 | 5/2018 |
| EP | 2729051 B1 | 6/2018 |
| EP | 3372910 A1 | 9/2018 |
| EP | 2058162 B1 | 1/2019 |
| EP | 2936362 B1 | 3/2019 |
| EP | 3578220 A1 | 12/2019 |
| EP | 3614946 A1 | 3/2020 |
| EP | 3616040 A1 | 3/2020 |
| EP | 3627261 A1 | 3/2020 |
| EP | 3634538 A1 | 4/2020 |
| EP | 3638557 A1 | 4/2020 |
| FR | 2865655 A1 | 8/2005 |
| FR | 2865655 B1 | 4/2006 |
| GB | 1270296 A | 4/1972 |
| IN | 201202311 P4 | 5/2013 |
| IN | 201504225 P4 | 7/2016 |
| IN | 205578306 U | 9/2016 |
| IN | 201647029095 A | 10/2016 |
| IN | 201721043516 A | 12/2017 |
| IN | 201947043607 A | 11/2019 |
| JP | 2-58091 A | 2/1990 |
| JP | 10104190 A | 4/1998 |
| JP | 2001095920 A | 4/2001 |
| JP | 3348956 B2 | 11/2002 |
| JP | 2004258828 A | 9/2004 |
| JP | 2005098571 A | 4/2005 |
| JP | 2006153337 | 6/2006 |
| JP | 2006153337 A | 6/2006 |
| JP | 2007508572 A | 4/2007 |
| JP | 4088313 B2 | 5/2008 |
| JP | 2008113861 A | 5/2008 |
| JP | 2008531218 A | 8/2008 |
| JP | 2008209094 A | 9/2008 |
| JP | 4469972 B2 | 6/2010 |
| JP | 2010119762 A | 6/2010 |
| JP | 2010287576 A | 12/2010 |
| JP | 2011075223 A | 4/2011 |
| JP | 2011520170 A | 7/2011 |
| JP | 5020358 B2 | 9/2012 |
| JP | 5250037 B2 | 7/2013 |
| JP | 5275955 B2 | 8/2013 |
| JP | 2013218725 A | 10/2013 |
| JP | 2014523038 A | 9/2014 |
| JP | 2014523039 A | 9/2014 |
| JP | 2014524797 A | 9/2014 |
| JP | 2014225236 A | 12/2014 |
| JP | 2015007083 A | 1/2015 |
| JP | 5711389 B2 | 4/2015 |
| JP | 2016033154 A | 3/2016 |
| JP | 2016509284 A | 3/2016 |
| JP | 2016197422 A | 11/2016 |
| JP | 2017503571 A | 2/2017 |
| JP | 2017508532 A | 3/2017 |
| JP | 6144238 B2 | 6/2017 |
| JP | 2017105839 A | 6/2017 |
| JP | 2017130833 A | 7/2017 |
| JP | 2017138567 A | 8/2017 |
| JP | 2017143589 A | 8/2017 |
| JP | 2017146065 A | 8/2017 |
| JP | 6203634 B2 | 9/2017 |
| JP | 06203634 B2 | 9/2017 |
| JP | 6252607 B2 | 12/2017 |
| JP | 06299785 B2 | 3/2018 |
| JP | 6310507 B2 | 4/2018 |
| JP | 2018511440 A | 4/2018 |
| JP | 2018122119 A | 8/2018 |
| JP | 6465155 B2 | 2/2019 |
| JP | 6483594 B2 | 3/2019 |
| JP | 2019082290 A | 5/2019 |
| JP | 6581667 B2 | 9/2019 |
| JP | 2019207684 A | 12/2019 |
| JP | 2020011074 A | 1/2020 |
| KR | 2009069335 A | 6/2009 |
| KR | 2014070553 A | 6/2014 |
| KR | 2014114422 A | 9/2014 |
| KR | 2015117092 A | 10/2015 |
| KR | 20150117092 A | 10/2015 |
| KR | 101816443 | 1/2018 |
| KR | 101816443 B1 | 1/2018 |
| KR | 2018009326 A | 1/2018 |
| KR | 101942785 B1 | 1/2019 |
| KR | 2019019180 A | 2/2019 |
| KR | 2019089405 A | 7/2019 |
| KR | 2019093380 A | 8/2019 |
| KR | 2019112507 A | 10/2019 |
| KR | 102072394 B1 | 2/2020 |
| KR | 2020031433 A | 3/2020 |
| KR | 102103631 B1 | 4/2020 |
| KR | 2020054445 A | 5/2020 |
| MX | 2010005090 A | 5/2010 |
| MX | 2014007304 A | 7/2014 |
| MX | 2015004842 A | 7/2015 |
| MX | 355476 B | 4/2018 |
| RU | 2015143725 A | 4/2017 |
| WO | 1997007439 A1 | 2/1997 |
| WO | 1998007930 A1 | 2/1998 |
| WO | 1998056488 A1 | 12/1998 |
| WO | 1998057165 A1 | 12/1998 |
| WO | 1999027483 A1 | 6/1999 |
| WO | 2001008752 A1 | 2/2001 |
| WO | 2004009161 A1 | 1/2004 |
| WO | 2005029452 A2 | 3/2005 |
| WO | 2005071372 A1 | 8/2005 |
| WO | 2006086415 A2 | 8/2006 |
| WO | 2006086472 A2 | 8/2006 |
| WO | 2006086522 A2 | 8/2006 |
| WO | 2006092635 A1 | 9/2006 |
| WO | 2006118654 A1 | 11/2006 |
| WO | 2007072385 A2 | 6/2007 |
| WO | 2013006627 A2 | 6/2007 |
| WO | 2007095266 A2 | 8/2007 |
| WO | 2008036159 A1 | 3/2008 |
| WO | 2008128250 A1 | 10/2008 |
| WO | 2008131338 A1 | 10/2008 |
| WO | 2009022320 A2 | 2/2009 |
| WO | 2009032540 A1 | 3/2009 |
| WO | 2009052704 A1 | 4/2009 |
| WO | 2009114249 A2 | 9/2009 |
| WO | 2009148646 A2 | 12/2009 |
| WO | 2010082322 A1 | 7/2010 |
| WO | 2011088539 A1 | 7/2011 |
| WO | 2011017778 A9 | 11/2012 |
| WO | 2012174420 A2 | 12/2012 |
| WO | 2013006615 A1 | 1/2013 |
| WO | 2013006632 A1 | 1/2013 |
| WO | 2013067223 A1 | 5/2013 |
| WO | 2013134645 A1 | 9/2013 |
| WO | 2013188013 A1 | 12/2013 |
| WO | 2014005106 A1 | 1/2014 |
| WO | 2014041104 A1 | 3/2014 |
| WO | 2014060726 A1 | 4/2014 |
| WO | 2014071145 A1 | 5/2014 |
| WO | 2014100687 A2 | 6/2014 |
| WO | 2014101824 A1 | 7/2014 |
| WO | 2015073459 A1 | 5/2015 |
| WO | 2015095532 A1 | 6/2015 |
| WO | 2015136502 A1 | 9/2015 |
| WO | 2015157575 A2 | 10/2015 |
| WO | 2016105552 A1 | 6/2016 |
| WO | 2016168119 A1 | 10/2016 |
| WO | 2016172469 A1 | 10/2016 |
| WO | 2016182853 A1 | 11/2016 |
| WO | 2017004068 A1 | 1/2017 |

(56) References Cited

FOREIGN PATENT DOCUMENTS

| WO | 2017004069 A1 | 1/2017 |
| WO | 2017029396 A1 | 2/2017 |
| WO | 2017101747 A1 | 6/2017 |
| WO | 2017106636 A1 | 6/2017 |
| WO | 2017106644 A1 | 6/2017 |
| WO | 2017126392 A1 | 7/2017 |
| WO | 2017141774 A1 | 8/2017 |
| WO | 2017218295 A1 | 12/2017 |
| WO | 2018016852 A1 | 1/2018 |
| WO | 2018044959 A1 | 3/2018 |
| WO | 2018200865 A1 | 11/2018 |
| WO | 2018201067 A1 | 11/2018 |
| WO | 2018209112 A1 | 11/2018 |
| WO | 2019008529 A1 | 1/2019 |
| WO | 2019202390 A1 | 10/2019 |
| WO | 2019236759 A1 | 12/2019 |
| WO | 2020023186 A1 | 1/2020 |
| WO | 2020037375 A1 | 2/2020 |
| WO | 2020041785 A1 | 2/2020 |
| WO | 2020042639 A1 | 3/2020 |
| WO | 2020086528 A1 | 4/2020 |

OTHER PUBLICATIONS

Office Action from U.S. Appl. No. 17/376,202 dated Jun. 7, 2023.
Office Action for Japanese Patent Application No. 2023-502667 dated Aug. 28, 2023, with English translation attached.
Invacare XPO2 Portable TM Portable Oxygen Concentrator Brochure, 2010, 4 pages.
Invacare Platinum Mobile POC1-100B, POC1-100C en Oxygen Concentrator User Manual, 2018, 160 pages.
Invacare SOLO2 TM Transportable Oxygen Concentrator User Manual, 2010, 52 pages.
Invacare Perfecto2 TM V Oxygen Concentrator Brochure, 2009, 2 pages.
Invacare Platinum™ 10L Oxygen ConcentratorIRC10LXO2 en HomeFill® System Compatible User Manual, 2016, 36 pages.
Invacare Platinum 10 Oxygen Concentrator Brochure, 2019, 2 pages.
International Search Report and Written Opinion from PCT/US21/41714 dated Nov. 15, 2021 (13 pages).
International Search Report and Written Opinion from PCT/US21/41710 dated Nov. 15, 2021 (16 pages).
International Search Report and Written Opinion from PCT/US21/41711 dated Oct. 21, 2021 (13 pages).
Chinh et al. "Simulation and Experimental Study of a Single Fixed-Bed Model of Nitrogen Gas Generator Working by Pressure Swing Adsorption", MDPI, Processes 2019, retrieved on Sep. 22, 2021, retrieved from <URL: https://www.mdpl.com/2227-9717/7/10/654/.
"RIDL, ""Audible Alerts and Visible Signals for the Inogen One GS"", Inogen One GS blog, Oct. 30, 2019. (12 pages)".
International Search Report and Written Opinion from PCT/US21/41717 dated Oct. 21, 2021.
International Search Report and Written Opinion from PCT/US2021/041718 dated Nov. 4, 2021.
International Search Report and Written Opinion from PCT/US2021/041712 dated Dec. 16, 2021.
Invitation to Pay Additional Fees from PCT/US21/41712 dated Oct. 6, 2021 (2 pages).
International Search Report and Written Opinion from PCT/US2021/041719 dated Oct. 27, 2021.
RIDL, "Audible Alerts and Visible Signals for the Inogen One G5", Inogen One G5 blog, Oct. 30, 2019, retrieved on Sep. 17, 2021, retrieved from <URL https://www.oxygenconcentratorstore.com/blog/inogen-g5-audible-alerts-and-visible-signals/>, entire document.
Office Action from U.S. Appl. No. 17/376,266 dated Oct. 12, 2023.

* cited by examiner

SYSTEM AND METHOD FOR CONCENTRATING GAS

This application claims priority to U.S. Prov. Pat. App. Ser. No. 63/052,533 titled "System and Method for Concentrating Gas" and filed on Jul. 16, 2020.

This application incorporates by reference the following patent applications: U.S. Prov. Pat. App. Ser. No. 63/052,694 titled "System and Method for Concentrating Gas"; U.S. Prov. Pat. App. Ser. No. 63/052,700 titled "System and Method for Concentrating Gas"; U.S. Prov. Pat. App. Ser. No. 63/052,869 titled "System and Method for Concentrating Gas"; U.S. Prov. Pat. App. Ser. No. 63/052,533 titled "System and Method for Concentrating Gas"; and U.S. Prov. Pat. App. Ser. No. 63/052,647 titled "System and Method for Managing Medical Devices", all filed on Jul. 16, 2020.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrating systems and methods, for example, are disclosed in U.S. Pat. Nos. 4,449,990, 5,906,672, 5,917,135, 5,988,165, 7,294,170, 7,455,717, 7,722,700, 7,875,105, 8,062,003, 8,070,853, 8,668,767, 9,132,377, 9,266,053, and 10,010,696 which are commonly assigned to Invacare Corporation of Elyria, Ohio and fully incorporated herein by reference.

Such systems are known to be either stationary, transportable, or portable. Stationary systems are intended to remain in one location such as, for example, a user's bedroom or living room. Transportable systems are intended to be moved from location to location and often include wheels or other mechanisms to facilitate movement. Portable systems are intended to be carried with the user such as, for example, via a shoulder strap or similar accessory.

In another aspect, these systems perform various startup and diagnostic tasks to ensure components are working satisfactorily. During some of these tasks, especially during warm-up, the user may not be aware of the status of the system, which can cause user confusion over system operability and availability. It is desirable to address these and other aspects of gas separating or concentrating systems.

SUMMARY

Gas concentrating systems and methods are provided. In one embodiment, status indications are provided to the user to indicate the status of the system. The indications include, for example, one or more displays for system warm-up, diagnostics, and/or alarms of various levels. In this manner, user confusion regarding the status of the gas separating system is minimized and/or eliminated.

BRIEF DESCRIPTION OF THE DRAWINGS

In the accompanying drawings which are incorporated in and constitute a part of the specification, embodiments of the inventions are illustrated, which, together with a general description of the inventions given above, and the detailed description given below, serve to example the principles of the inventions.

DESCRIPTION

As described herein, when one or more components are described or shown as being connected, joined, affixed, coupled, attached, or otherwise interconnected, such interconnection may be direct as between the components or may be indirect such as through the use of one or more intermediary components. Also, as described herein, reference to a member, component, or portion shall not be limited to a single structural member, component, element, or portion but can include an assembly of components, members, elements, or portions.

Embodiments of the present inventions provide, for example, the ability to provide an indication or status of the gas separating or concentrating system. The systems often perform tasks such as warm-up or start up procedures and diagnostics that may cause user confusion regarding the operability of the system. An indication or status of the system during these tasks or procedures is provided to the user so the user may better understand the status of the system. In one embodiment, the status indications are visual indications provided on a display panel. The indications can be in the form of graphics, displays, and/or icon. In one embodiment, the indications are illuminated by light emitting devices such as light emitting diodes, lamps, LCD, OLED, AMOLED, LED, 4K, 2K, FullHD, HD, etc. technology. In other embodiments, the indications use color in association with each segment, dot, or pixel of the display. These colors can be any colors including red, yellow, green, orange, blue, and combinations and/or sequences of the same. In another embodiment, the indications are highly visible and simple to understand. In yet other embodiments, the indications can further include audible signals including, for example, one or more audible tone(s), beeps, or other sounds. In one exemplary embodiment, a status display is provided with the ability to show, for example, good operation, low priority alarm(s), high priority alarm(s), and/or warm-up status using the same over all display or display icon.

Figure 1:
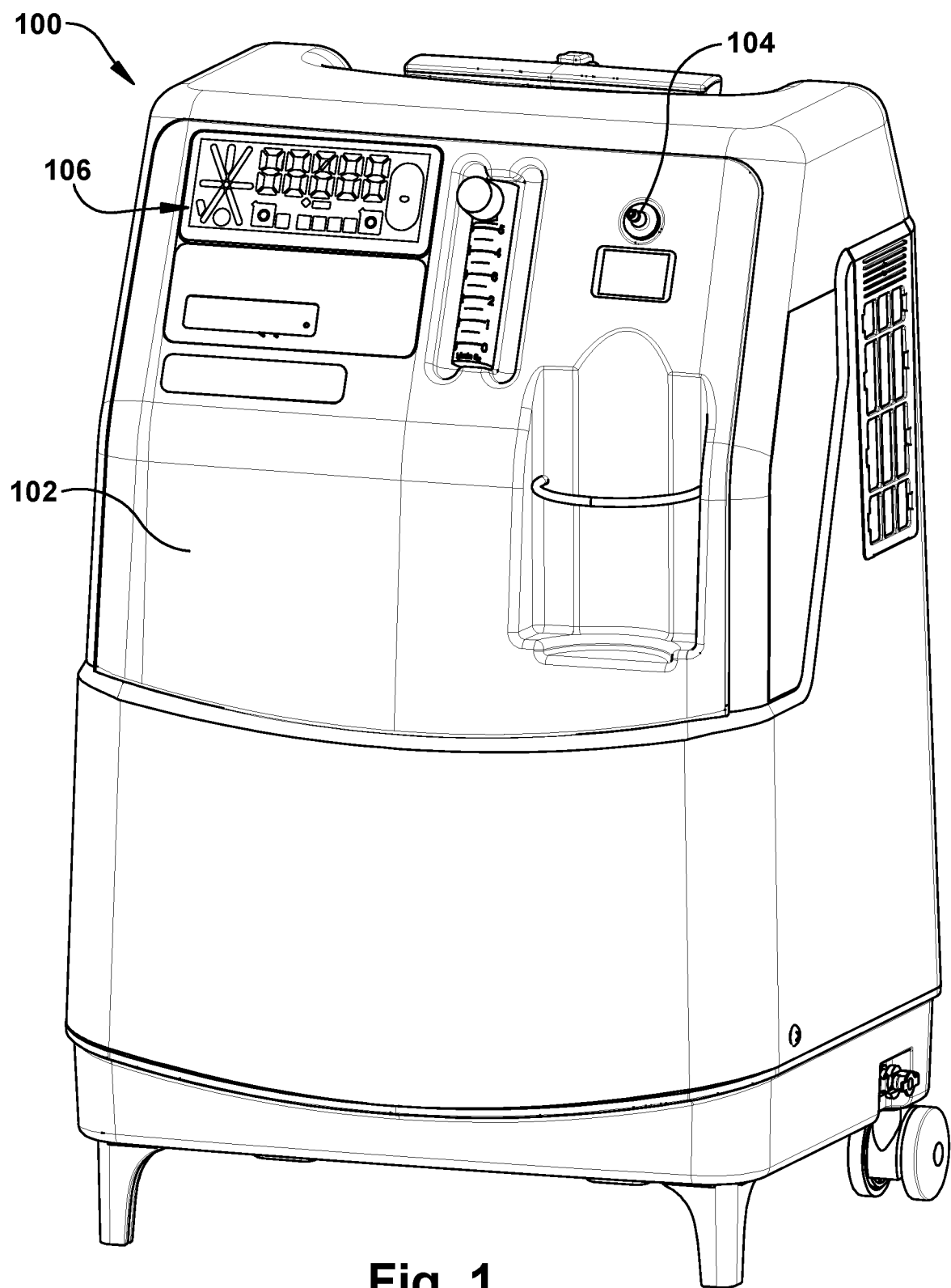
FIG. 1 shows one embodiment of the gas concentrating system.

Illustrated in FIG. 1 is one embodiment of an oxygen system 100. The system may be stationary such as, for example, for use in a hospital or a patient's home. The system can also be ambulatory or mobile such as, for example, for use by a patient when they are away from home. The system can be configured in a manner to allow the patient to carry the system such as, for example, through an over the shoulder strap or through an arrangement whereby the system includes a handle and wheels. Other mobility configurations are also included.

Oxygen system 100 includes a housing 102, which can be in one or more sections. Housing 102 includes a plurality of openings for the intake and discharge of various gases such as, for example, the intake of room air and the discharge of nitrogen and other gases. Oxygen system 100 generally intakes room air, which is mostly comprised of oxygen and nitrogen, and separates the nitrogen from the oxygen. The oxygen is stored in one or more internal or external storage or product tanks and the nitrogen is discharged back into the room air. For example, the oxygen gas may be discharged through port 104 to a patient through tubing and nasal cannula. Alternatively, the oxygen gas may be discharged through a supplemental port to an oxygen cylinder filling device, such as HOMEFILL® that is manufactured by Invacare Corp. of Elyria, Ohio, USA.

Oxygen system 100 further includes a display 106 for conveying the status of the system to a user (and also to service personnel). Status display 106 is located proximate the top portion of housing 102 where it can be easily seen. Display 106 is also of significant size and dimension to provide good visibility. For example, in one embodiment display 106 as a height of approximately 2 inches and a length of approximately 5 inches. Other size dimensions are also possible in keeping with providing good visibility. As will be described in more detail, display 106 provides various indications of system status including, for example, static and animated displays.

Figure 2:
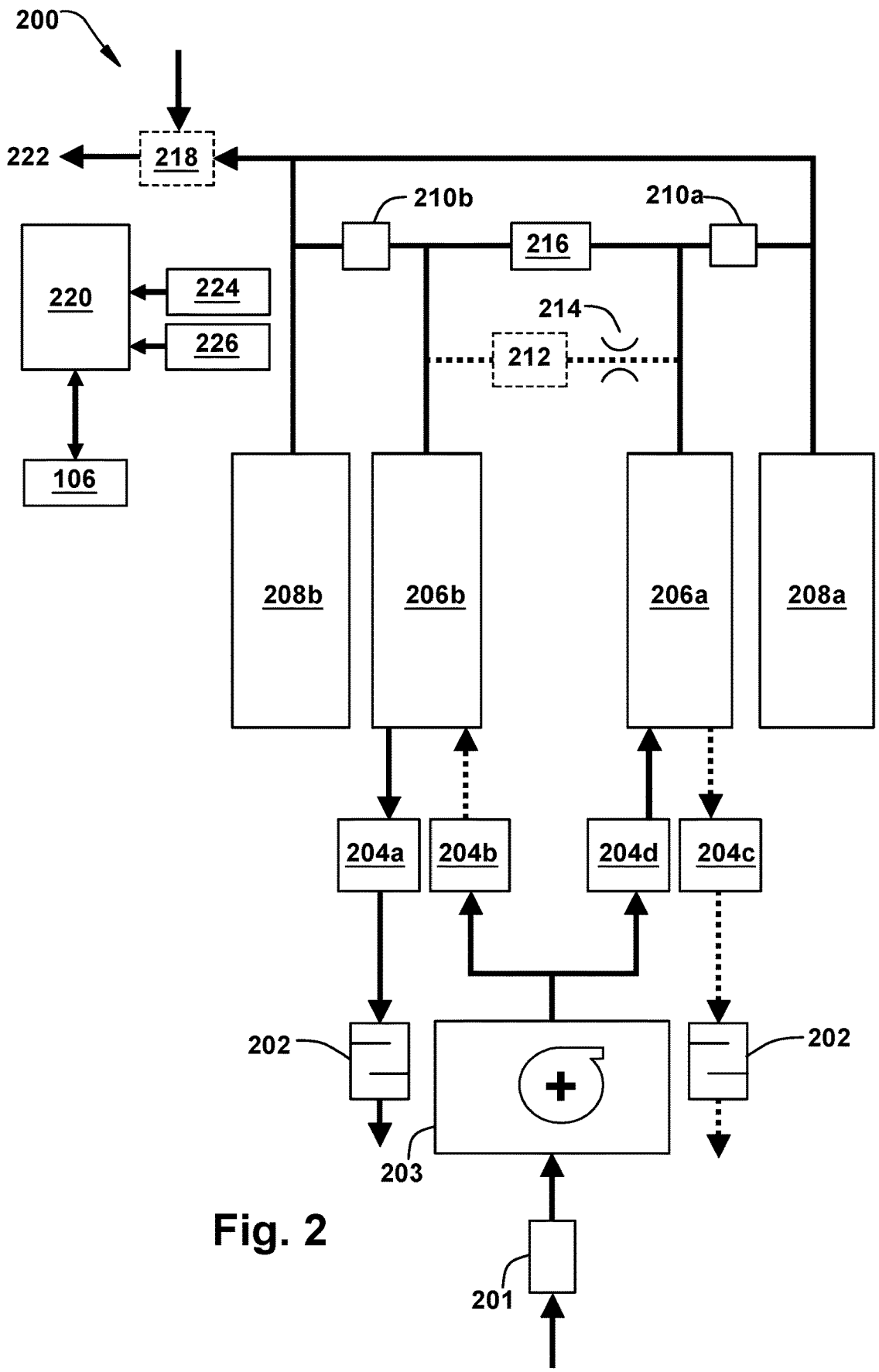
FIG. 2 is one embodiment of a pneumatic block diagram of a gas concentrating system.

FIG. 2 illustrates one embodiment of an exemplary pneumatic block diagram for a gas concentrating system and method using pressure swing adsorption (PSA). The system and method can include multiple gas separation sieve beds 206a and 206b, multiple valves 204a, 204b, 204c, and 204d, one or more product tanks 208a, 208b and a conserver valve/device 218. In this embodiment, product tanks 208a, 208b are shown connected so they act as one product tank but may also be arranged to act as two product tanks. The system also includes compressor/pump 203 and one or more filters 201 and mufflers 202.

Sieve beds 206a and 206b are filled with a physical separation medium or material. The separation material selectively adsorbs one or more adsorbable components and passes one or more nonadsorbable components of a gaseous mixture. Generally, the physical separation material is a molecular sieve with pores of uniform size and essentially the same molecular dimensions. These pores selectively adsorb molecules in accordance with molecular shape, polarity, degree of saturation, and the like. In one embodiment, the physical separation medium is an aluminasilicate composition with 4 to 5 ANG. (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13x zeolite. The zeolite adsorbs nitrogen, carbon monoxide, carbon dioxide, water vapor, and other significant components of air. Other types of separation media may also be used. Also, more than two sieve beds can be used. In other embodiments, the sieve beds 206a and 206b can be structurally integrated with one or more product tanks 208a and 208b, such as described in U.S. Pat. No. 8,668,767, which is hereby fully incorporated by reference for this and other features.

In operation, as shown by the solid lines in FIG. 2, during an exemplary fill cycle of separation bed 206a, pump/compressor 203 draws room air through filter 201 and to valve 204d and separation bed 206a, which produces oxygen at its output and into product tanks 208a, 208b through valve 210a. Pump/compressor 203 supplies air up to about 32 pounds per square inch during the fill phase to a sieve bed. Other working pressure ranges including about 15-32 pounds per square inch. Valves 210a and 210b may be check valves or any other similarly functioning valve that allows only one-way flow.

While separation bed 206a is undergoing the fill cycle, separation bed 206b may be undergoing a purge cycle to expel any nitrogen gas from a previously fill cycle. During the purge cycle, previously pressurized separation bed 206b expels nitrogen gas through valve 204a and out to atmosphere through muffler 202. During the purge cycle, an amount of oxygen from separation bed 206a or product tanks 208a, 208b can be fed into separation bed 206b to preload or pre-charge the separation bed 206b with oxygen, as controlled by optional bleed valve 212 and fixed orifice 214, shown in FIG. 2 with dashed lines.

As shown by the dotted lines in FIG. 2, once separation bed 206a has been filled and/or separation bed 206b has been purged, control system 220 switches valves 204a, 204b, 204c, and 204d so that separation bed 206b enters the fill cycle while separation bed 206a enters the purge cycle. In this state, pump 203 directs room air into separation bed 206b, which produces oxygen at its output and into product tanks 208a, 208b through valve 210b. During the purge cycle, an amount of oxygen from separation bed 206b or product tanks 208a, 208b can be fed into separation bed 206a to preload or pre-charge the separation bed 206a with oxygen, now flowing in the opposite direction as compared to the previous cycle. The illustrated system also includes an exemplary pressure equalization valve 216, which equalizes the pressure in the two separation beds prior to a purge/fill cycle change.

The pressure equalization valve 216 can allow for a more efficient generation of oxygen by equalizing the pressure between the outputs of a separation bed (e.g., 206a) nearing the end of its fill cycle and a separation bed (e.g., 206b) nearing the end of its purge cycle. For example, pressure equalization valve 216 may be activated to equalize the pressure between the outputs of separation bed 206a and separation bed 206b near the end of each purge/fill cycle. U.S. Pat. Nos. 4,449,990 and 5,906,672, which are fully incorporated herein by reference, further describe the operation of pressure equalization valves. In this manner, each separation bed 206a, 206b cyclically undergoes alternating fill and purge cycles as controlled by control system 220 to generate oxygen.

As shown in FIG. 2, optional conserver valve/device 218 may be used to control the delivery of product gas to a user 222. Conserver valve may switch between providing concentrated product gas from the product tanks 208a, 208b or venting to the room air. For example, the conserver valve may be used to selectively provide various continuous or pulsed flows of oxygen concentrated product gas in an amount and at a time determined by the control system 220. This time is typically based on sensing an inhalation by the user and is typically determined by sensing a drop in pressure or (increase in flow) proximate the user's nose or mouth.

In this embodiment, control system 220 may utilize various control schemes to optimize the production and delivery of concentrated product gas by controlling the activation, levels, and relative timing of pressure source 203 and valves 204a, 204b, 204c, 204d, 216, and 212, for example. This is accomplished by use of one or more pressure sensor(s) 224 and/or oxygen concentration sensor(s) 226. In one embodiment, pressure and oxygen sensors 224 and 226 monitor the pressure and oxygen concentration entering product tank(s) 208a and 208b. In other embodiments, use of timed cycles can be employed wherein the cycle times are set at the factory. In other embodiments, the cycle times can be determined from flow settings and/or sensed patient flow demands.

While FIG. 2 illustrates a pressure swing adsorption (PSA) cycle, other gas concentrating cycles may also be used including vacuum swing adsorption (VSA), vacuum— pressure swing adsorption (VPSA) or other similar modes. The particular gas concentrating mode is not critical to the embodiments of the invention described herein so long as they are capable of producing a concentrated gas such as oxygen to the user. Examples of the above modes of operation are disclosed and, for example, U.S. Pat. Nos. 9,266,053 and 9,120,050 which have been fully incorporated by reference.

During startup, the system and method shown and described in FIG. 2 may undergo diagnostics and several fill and purge cycles to ensure proper operability. This startup process may create user confusion as to whether the system is properly operating. Further, the failure of one or more of the system's working components can result in inoperability or significantly impaired operability of the system. In these and other situations, display 106 can provide a visual indication of the system status to help the user and/or service personnel. As shown in FIG. 2, controller 220 communicates with display 106 to generate visual and/or audible system status indications. Controller 220 is preferably microprocessor-based and executes software instructions or logic stored in memory associated therewith.

Figure 3A:
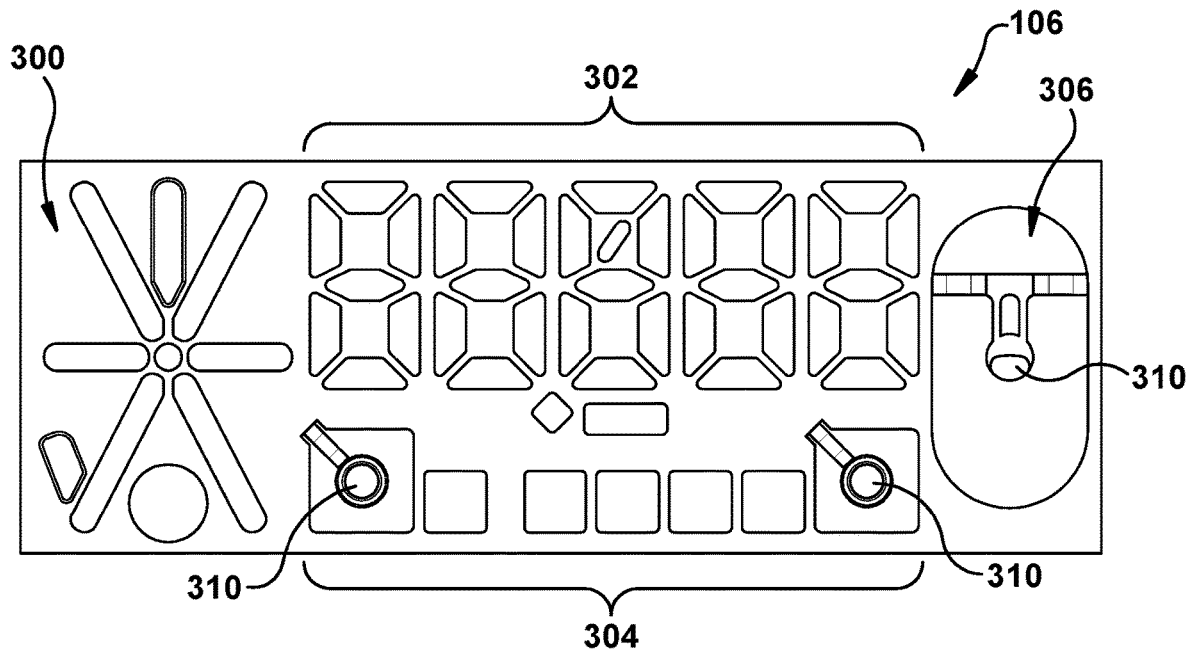
FIGS. 3A-3B show one embodiment of a status display for a gas separation or concentrating system.
Figure 3B:
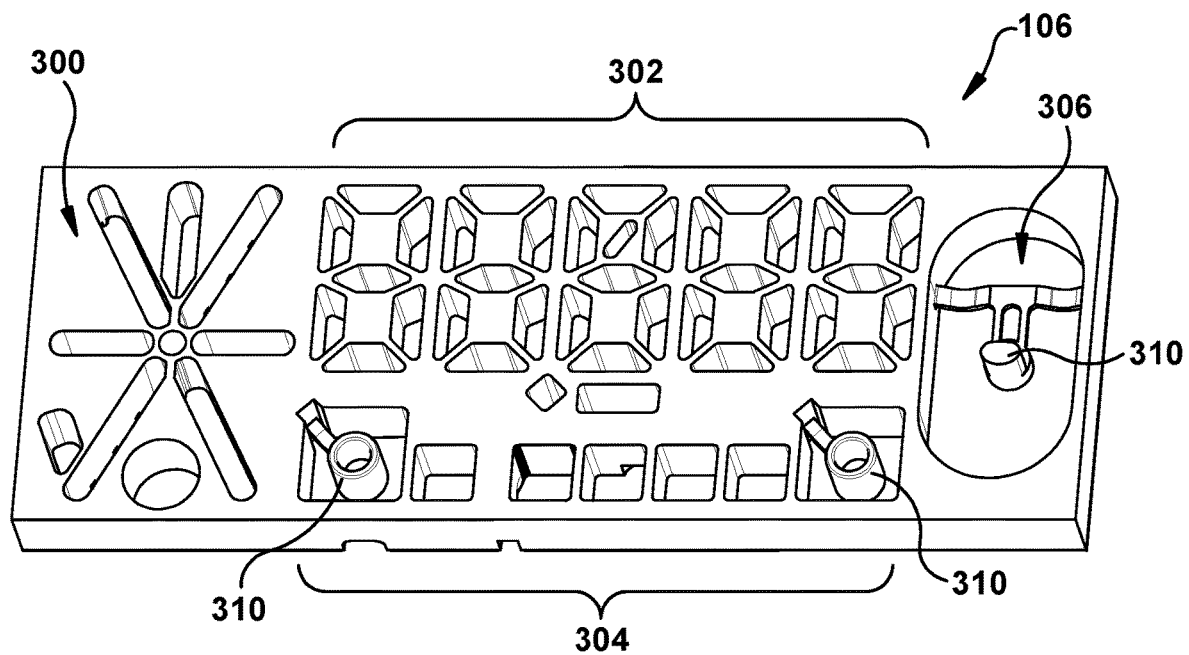

Referring now to FIGS. 3A-3B, one embodiment of a display 106 is shown. In this embodiment, display 106 includes a body having various display portions. These include display portions 300, 302, 304, and 306. Each of these display portions can include one or more light emitting or illumination devices. Furthermore, in this embodiment, the body includes one or more depressible buttons 310 in various display portions (e.g., 304 and 306). These buttons allow the display portions to also function as inputs to the system controller 220.

In the embodiment shown, display portion 300 is a multi-segment graphical display. Display portion 302 is a multi-segment alphanumerical display. Display portion 304 includes a plurality of icon displays and one or more buttons 310. Display portion 306 also includes at least one icon display and button 310. In other embodiments, display portion 300 can be used by itself (as shown in FIGS. 5A-5G, and 6-8) and without the need for or combination with other displays. In yet other embodiments, more or less displays (e.g., displays 302, 304, and 306) can be used and the display 106 of FIGS. 3A-3B is just one illustrated embodiment.

Figure 4:
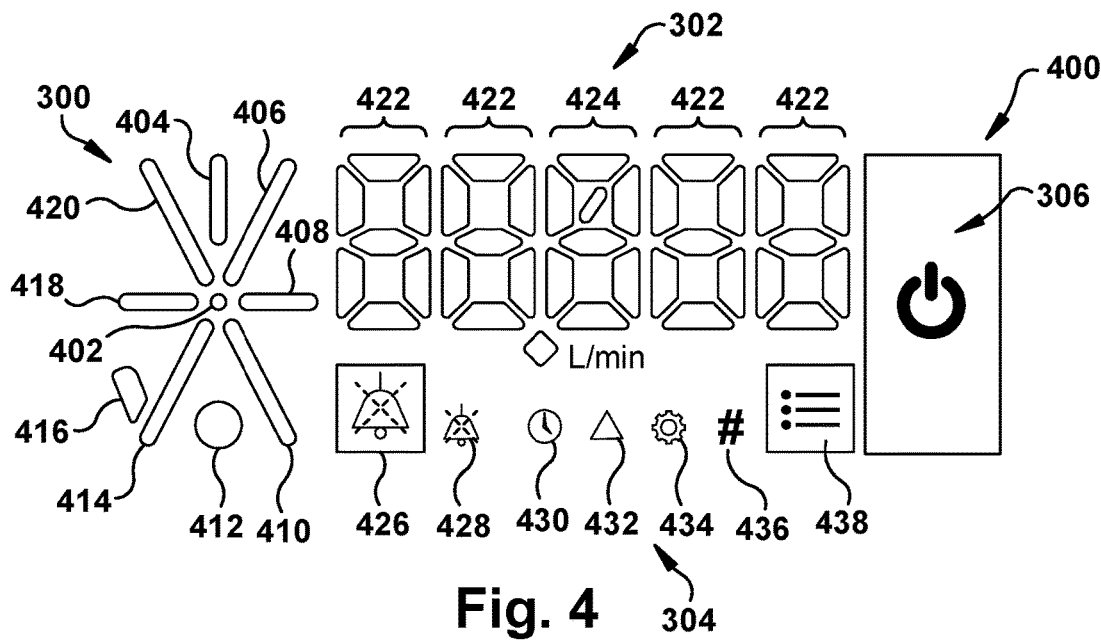
FIG. 4 shows another embodiment of a status display for a gas separation or concentrating system.

FIG. 4 illustrates one embodiment 400 of the illuminable displays that can be used indicate system status. For example, display portion 300 can include a plurality of illuminable segments arranged in a radiating or star pattern. This includes segments 404, 406, 408, 410, 412, 414, and 418. At the center of the arrangement, segment 402 can be provided. Further yet, a segment 412 can be provided near the bottom of display portion 300 and a slanted segment 416 can also be provided near the bottom of display portion 300. While display portion 300 has been shown with 7 segments arranged in a radiating or star pattern, more or less than 7 segments can also be used. Further, the space between illuminated segments is non-illuminable in this embodiment. In other embodiments, this space can be illuminable via one or more additional segments.

Display portion 302 includes a plurality of illuminable segments 422 and 424. The segments are arranged to provide an alpha-numerical display. Segments 422 include a seven-segment array of illuminable elements. Segment 424 includes an eight-segment array of illuminable elements. While display portion 302 has been shown with seven and eight-segment arrays of illuminable elements, more or less than these numbers of segment displays can also be used. Display portion 302 can display information such as flow rates (e.g., liters per minute (L/min)), pressure, oxygen concentration, diagnostic and/or error codes, messages, operational modes, etc.

Display portion 304 includes a plurality of illuminable icons. Icons 426 and 428 indicate audio pause (426 is an input button and 428 is the icon that is illuminated when the button is pressed). Icon 430 indicates lifetime hours/user hours, which are provided on display 302. Icon 432 indicates warning/error codes exist and can be provided on display 302. Icon 434 indicates firmware version, which can be provided on display 302. Icon 436 indicates serial number, which can also be provided on display 302. Icon 438 indicates menu button, which is used to step through illuminable icons 430-436. Icons 426 and 438 also overlay depressible buttons (see FIGS. 3A-3B). These buttons function to audio pause (silence active alarms) and scroll though the different information corresponding with icons 430-436.

Display portion 306 includes a large icon for power indication (e.g., does the unit have power (i.e., plugged into a live outlet and the rocker switch in the base is in the on position) and illuminates when power is applied to the unit)) indication and input. The on/off function should be easily locatable and easily depressible. As shown in FIGS. 3A-3B, button 310 underlies the icon display and allows a user to provide input to the controller to turn on and off the system.

Figures 5A, 5B, 5C, 5D:
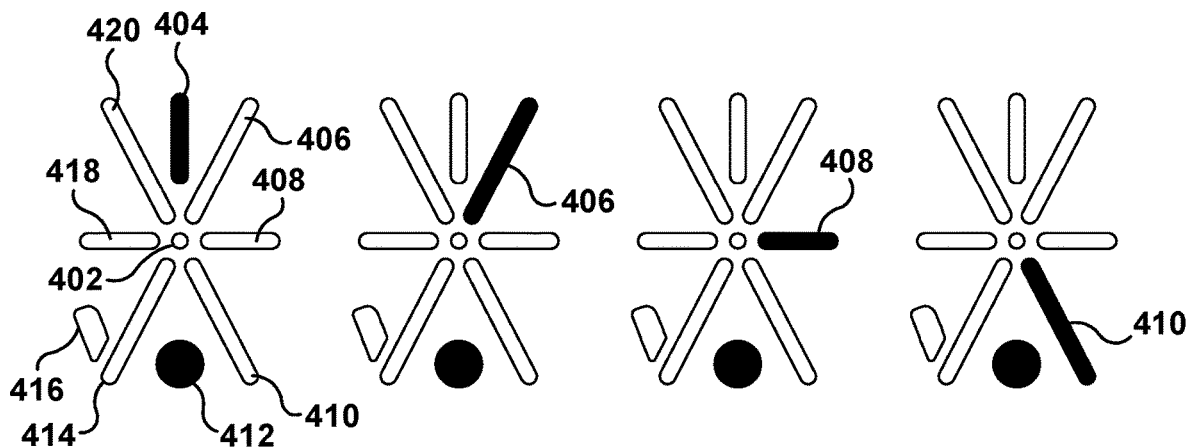
FIGS. 5A-5G shows one embodiment of a sequence of status displays indicating, for example, a warm-up or start-up status indication.
Figures 5E, 5F, 5G:
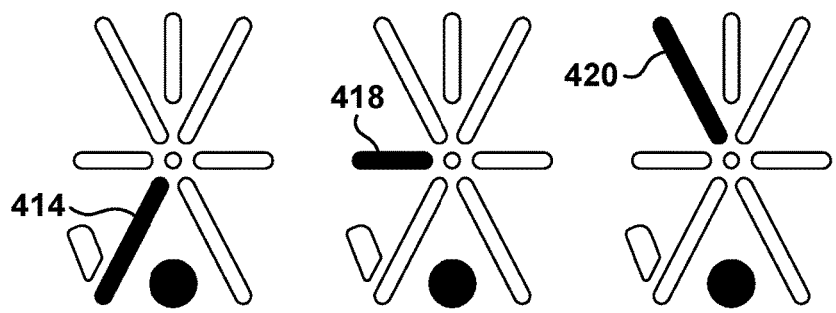

Referring now to FIGS. 5A-5G, one embodiment of display portion 300 providing a sequence of displays to indicate a system warm up or start up procedure is shown. The sequence of displays includes illuminating each segment in a manner to provide a rotating order around a central point. As shown in FIGS. 5A-5G, each segment of display portion 300 is turned on and then off as the next segment is illuminated. For example, as shown in FIG. 5A, the sequence of displays can begin by turning on or illuminating segment 404 while all other segments are turned off. In other embodiments, vertical segment 404 does not need to be the first segment illuminated. Instead, the sequence can begin with segment 406 or any other segment. Thereafter, as shown in FIG. 5B, segment 404 is turned off and segment 406 is turned on. As shown in FIGS. 5C-5G, the remaining segments (e.g., 408, 410, 414, 418, and 420) are turned on and off in sequence. The result of the sequences displays a rotating order around a central point (e.g., segment 402) to indicate the system is working and warming up (e.g., to provide therapeutic oxygen). The rotating order display can resemble the second hand of a clock to indicate to the user the system is in the start-up or warm-up sequence. A further segment 412 can be illuminated with the colors blue and/or green color to indicate the non-fault or non-alarm nature of the rotating order display. Other colors can also be used including, for example, green for normal operation, yellow for warning, red for shutdown error, and blue for warm-up. The segments could also be illuminated in these colors with or without illuminating segment 412. In other embodiments, the rotating order display can be generated using segments arranged in patterns other than radiating or star. For example, a multi-segment circumferential display can be used and the display sequence can be the incremental turning on and off of the circumferential display segments. In yet other embodiments, all the segments may be illuminated or turned on and the rotating order is generated by sequentially turning off a display segment. Further yet, the rotating order display can be generated by a build-up and reduce-down sequence. In the build-up sequence, all the segments are initially turned off and each segment is illuminated one by one until all segments are illuminated. In the reduce-down sequence, all the segments are illuminated and each segment is turned off one by one until all the segments are turned off. The build-up and reduce-down sequence can then repeat. Other examples of sequences are also possible.

Figure 6:
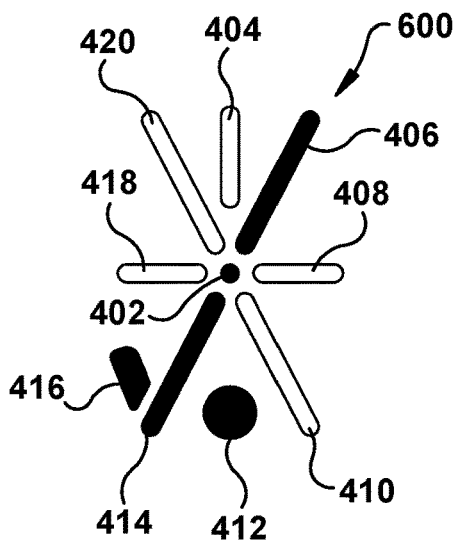
FIG. 6 illustrates one embodiment of a status display meaning the status is good, acceptable and/or within operating parameters or range.

FIG. 6 illustrates another embodiment of display portion 300 generating a positive confirmation display 600. In this embodiment, segments are illuminated to generate a checkmark "√" symbol. Segments 406, 402, 414, and 416 can be illuminated to generate the checkmark status display. The checkmark status display can be used to indicate, for example, the oxygen production status (e.g., greater than 85% purity) of the system after startup or warm-up, or at other times. Segment 412 can also be illuminated with a green color to further signify a positive status. In other embodiments, segments 416, 414, 402, and 406 can also be green and illumination of segment 412 can be omitted. The omission of segment 412 can be carried across the board for all exemplary segment configurations described herein.

Figure 7:
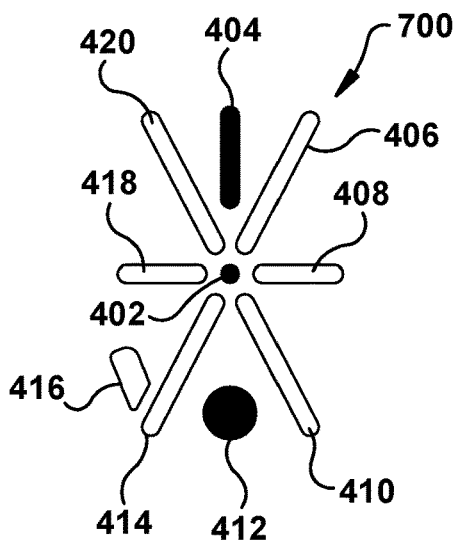
FIG. 7 shows one embodiment of a status display signifying a low and/or medium level alarm indication.

FIG. 7 illustrates another embodiment of display portion 300 generating a low level or low priority alarm display 700. In this embodiment, segments are illuminated to generate an exclamation mark "!" symbol. Segments 404, 402, and 412 can be illuminated to generate the exclamation mark display. In this embodiment, segment 412 can be further illuminated with a yellow color to indicate the low level or priority of alarm. Such an alarm can be generated when, for example, the oxygen purity has fallen below 85% such as between 73% to 85%, or other range. The exclamation mark display of FIG. 7 can be made to flash to indicate, for example, a sensor failure has occurred. Other system status conditions may also be indicated by the exclamation mark display of FIG. 7 including, for example, low flow alarm due to a pinched cannula or other reason.

Figure 8:
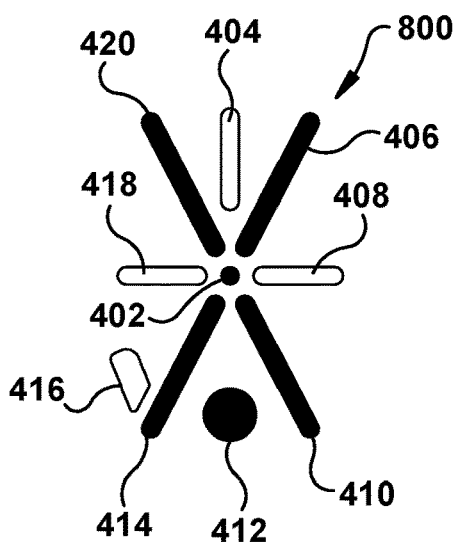
FIG. 8 shows one embodiment of a status display signifying a high-level alarm indication.

FIG. 8 illustrates another embodiment of display portion 300 generating a high-level or high-priority alarm display 800. In this embodiment, segments are illuminated to generate an "X" symbol. Segments 420, 406, 410, 414 and 402 can be illuminated to generate the exclamation mark display. In this embodiment, segment 412 can be further illuminated with a red color to indicate the high-level or priority of alarm. Such an alarm can be generated when, for example, the oxygen purity has fallen below 73% (or other value). The "X" symbol display of FIG. 8 can be made to flash to indicate, for example, a unit shutdown due to a component failure or other reason. Other system status conditions may also be indicated by the "X" symbol display of FIG. 8 including, for example, a unit shutdown due to the unit being operated in an environment that can cause the unit to overheat.

In other embodiments, display segments 402-420 can illuminate in different colors (e.g., blue, green, yellow, orange, red, etc.) based on the type of alarm present and/or in association with the color of illuminated display segment 412. For example, illuminated display segment 412 can be illuminated blue during warmup, green when the system is operating normally, yellow when there is a non-shutdown error, and red when a shutdown error has occurred. Further, the checkmark "√" display of FIG. 6 can have segments illuminated in blue color during warmup and green during normal operation. The exclamation mark "!" display of FIG. 7 can have segments illuminated in yellow color when there is a non-shutdown error and the "X" symbol display of FIG. 8 can be illuminated in the red color when a shutdown error has occurred. Hence, multi-color segments can be used to illuminate the displays.

Figure 9:
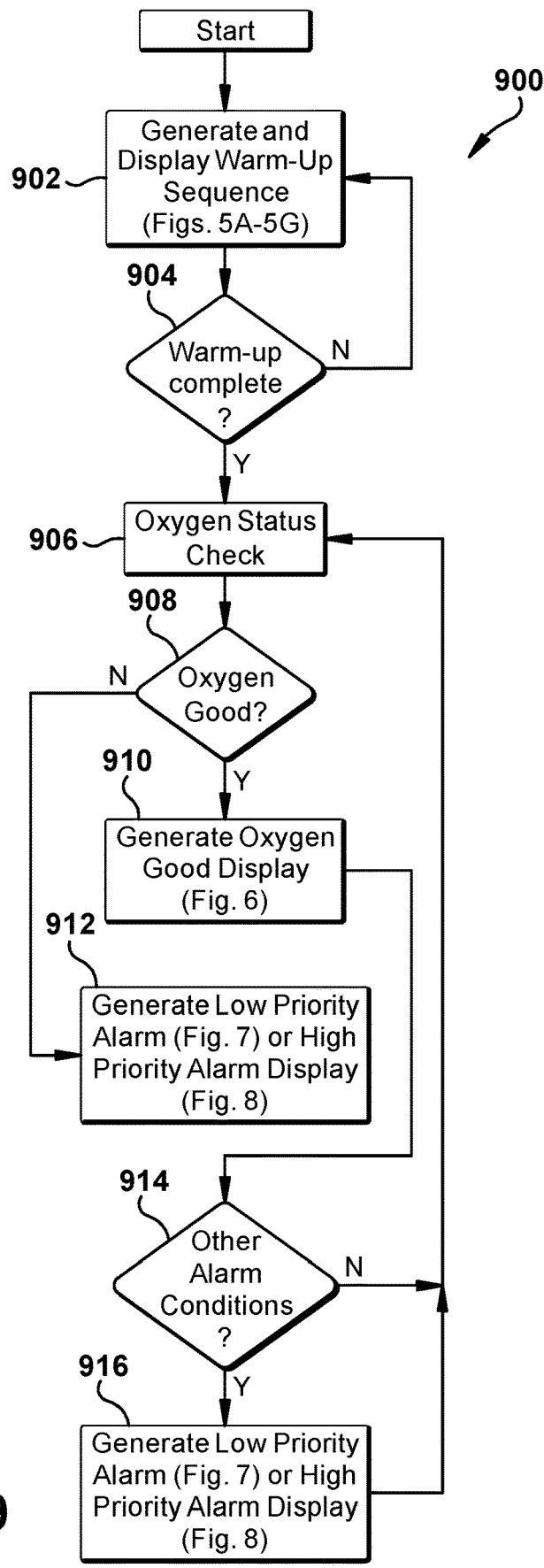
FIG. 9 illustrates one embodiment of controller logic for generating one or more status indications and/or displays.

Referring now to FIG. 9, one embodiment of a flow chart or logic 900 for a gas concentrating system is illustrated. The rectangular elements denote processing blocks and represent computer software instructions or groups of instructions. The diamond elements represent decision processing blocks and computer software instructions or groups of instructions. The flow diagram(s) shown and described herein do not depict syntax of any particular programming language. Rather, the flow diagram(s) illustrate the functional information that may be used to fabricate circuits or computer software to perform the processing of the system. It should be noted that many routine program elements, such as initialization of loops and variables and the use of temporary variables are not shown. Furthermore, the exact order of the process steps need not necessarily be performed in the order shown or described herein and may be modified to exclude or add certain steps.

In block 902, the controller performs a start-up or warm up sequence after it is turned on and generates, for example, the warm-up/start-up sequence of displays shown in FIGS. 5A-5G. In block 904, the logic determines if the system warm-up process is complete. If not, the controller loops back to block 902 and continues to generate and display the warm-up sequence of FIGS. 5A-5G. If the system warm-up process is complete, the logic advances to block 906 where the oxygen purity or content of the system is checked by reading oxygen values from, for example, oxygen sensor 226. In other embodiments, the system can read or measure other parameters (e.g., nitrogen content, compressor motor current, voltage, performance, etc., valve signal levels, product tank pressure decay, etc.) to determine system status. Block 908 determines if the oxygen purity is acceptable. If the oxygen purity is acceptable (e.g., above 85% or some other value), the logic advances to block 910 and generates the checkmark display of FIG. 6. If the oxygen purity is between, for example, 73% to 85% (or some other range), the logic advances to block 912 and generates a low priority alarm as shown in, for example, FIG. 7. If the oxygen purity is below, for example, 73% (or some other value), the logic advances to block 912 and generates a high priority alarm as shown in, for example, FIG. 8. In block 914, the logic checks for other alarm conditions and proceeds to block 916 to generate low priority alarms (e.g., FIG. 7) and/or high-priority alarms (e.g., FIG. 8). The logic may run as a continuous loop, intermittently, or at a predetermined time(s) during operation of the system.

Configured as such, status indications are provided to the user to indicate the status of the system. The indications include, for example, one or more displays for system warm-up, diagnostics, and/or alarms of various levels. In this manner, the user and service personnel can be informed regarding the status of the gas separating system. Furthermore, the displays are large and highly visible to assist in their recognition and attention.

While the present inventions have been illustrated by the description of embodiments thereof, and while the embodiments have been described in considerable detail, it is not the intention of the descriptions to restrict or in any way limit the scope of the inventions to such detail. Additional advantages and modifications will readily appear to those skilled in the art. Therefore, the inventions, in their broader aspects, are not limited to the specific details, the representative apparatus, and illustrative examples shown and described. Accordingly, departures can be made from such details without departing from the spirit or scope of the general inventive concepts.

What is claimed:

1. A gas concentrating system comprising:
   a controller;
   a display in communication with the controller; the display comprising:
      a plurality of illuminable segments arranged in a radiating pattern; and
   logic illuminating at least one of the plurality of illuminable segments according to one of a plurality of patterns based on system status; and
   wherein one of the plurality of patterns comprises a display that the system is within acceptable operating parameters.

2. The system of claim 1, wherein one of the plurality of patterns comprises illuminating the plurality of segments to form a rotating display during system startup.

3. The system of claim 1, wherein the display that the system is within acceptable operating parameters comprises a checkmark display.

4. A gas concentrating system comprising:
   a controller;
   a display in communication with the controller; the display comprising:
      a plurality of illuminable segments arranged in a radiating pattern;
   logic illuminating at least one of the plurality of illuminable segments according to one of a plurality of patterns based on system status; and
   wherein one of the plurality of patterns comprises an alarm display that the system is not within acceptable operating parameters.

5. The system of claim 4, wherein the alarm display comprises an exclamation mark display.

6. The system of claim 4, wherein the alarm display comprises an X mark display.

7. A gas concentrating system comprising:
   a controller;
   a display in communication with the controller; the display comprising:
      a plurality of illuminable segments arranged in a radiating pattern;
   logic illuminating at least one of the plurality of illuminable segments according to one of a plurality of patterns based on system status; and
   logic for reading an oxygen concentration of the system as a status indicator.

8. A gas concentrating system comprising:
   a controller;
   a display in communication with the controller; the display comprising:
      a plurality of illuminable segments arranged in a radiating pattern;
   logic illuminating at least one of the plurality of illuminable segments according to one of a plurality of patterns based on system status; and
   wherein the display further comprises at least one illuminable segment proximate the center of the radiating pattern.

9. The system of claim 1, wherein the illuminable segments are elongated.

10. The system of claim 1 wherein at least one of the plurality of illuminable segments is a multi-color segment.

11. A gas concentrating system comprising:
    a controller;
    a display in communication with the controller; the display comprising:
       a plurality of illuminable segments arranged in a radiating pattern;
    logic illuminating the plurality of illuminable segments according to one of a plurality of patterns indicating system status; and
    wherein one of the plurality of patterns comprises a checkmark display indicating normal system operation.

12. The system of claim 11, wherein one of the plurality of patterns comprises a rotating display indicating system warmup.

13. A gas concentrating system comprising:
    a controller;
    a display in communication with the controller; the display comprising:
       a plurality of illuminable segments arranged in a radiating pattern;
    logic illuminating the plurality of illuminable segments according to one of a plurality of patterns indicating system status; and
    wherein one of the plurality of patterns comprises an exclamation mark display indicating an alarm.

14. A gas concentrating system comprising:
    a controller;
    a display in communication with the controller; the display comprising:
       a plurality of illuminable segments arranged in a radiating pattern;
    logic illuminating the plurality of illuminable segments according to one of a plurality of patterns indicating system status; and
    wherein one of the plurality of patterns comprises an X mark display indicating an alarm.

15. A gas concentrating system comprising:
    a controller;
    a display in communication with the controller; the display comprising:
       a plurality of illuminable segments arranged in a radiating pattern;
    logic illuminating the plurality of illuminable segments according to one of a plurality of patterns indicating system status; and
    logic for reading an oxygen concentration and determining if the oxygen concentration is below a threshold.

16. A method of displaying one or more status indications for a gas concentrating system, the method comprising:
    illuminating during system warmup one or more segments of a plurality of illuminable segments in a rotating pattern;
    reading an oxygen concentration; and
    based on the read oxygen concentration level, illuminating one or more segments of the plurality of illuminable segments to display one of a plurality of status indications.

17. The method of claim 16, wherein illuminating one or more segments of the plurality of illuminable segments to display one of a plurality of status indications comprises illuminating the segments to display a normal status indication if the oxygen concentration level is above a threshold.

18. The method of claim 16, wherein illuminating one or more segments of the plurality of illuminable segments to display one of a plurality of status indications comprises illuminating the segments to display a low priority alarm status indication if the oxygen concentration level is below a threshold.

19. The method of claim 16, wherein illuminating one or more segments of the plurality of illuminable segments to display one of a plurality of status indications comprises illuminating the segments to display high priority alarm status indication if the oxygen concentration level is below a threshold.

20. The method of claim 16 wherein illuminating one or more segments of the plurality of illuminable segments to display one of a plurality of status indications comprises illuminating the one or more segments a plurality of colors.

* * * * *